United States Patent [19]

Freeman et al.

[11] Patent Number: 4,902,615

[45] Date of Patent: Feb. 20, 1990

[54] DETECTION OF HUMAN CANCER CELLS WITH ANTIBODIES TO HUMAN CANCER NUCLEOLAR ANTIGEN P120

[75] Inventors: James W. Freeman; Harris Busch, both of Houston, Tex.

[73] Assignee: Biosciences Corporation of Texas, Richardson, Tex.

[21] Appl. No.: 32,007

[22] Filed: Mar. 27, 1987

[51] Int. Cl.$^4$ .................. G01N 33/53; G01N 33/577; C12N 15/00; C12N 1/00

[52] U.S. Cl. ........................................ 435/7; 424/6; 435/172.2; 435/240.27; 435/810; 435/70.21; 436/503; 436/508; 436/548; 436/808; 436/813; 530/350; 530/413; 530/417; 530/387; 935/108; 935/110

[58] Field of Search ................. 435/7, 810, 68, 172.2, 435/240.27; 436/506, 508, 514, 547, 548, 813, 543, 503, 518; 424/9, 106; 530/828, 846, 809, 387, 412, 413, 416, 417; 935/108, 110

[56] References Cited

U.S. PATENT DOCUMENTS 4,448,890  5/1984  Smetana et al. ............... 436/508
4,725,669  2/1988  Essex et al. ................... 530/322

OTHER PUBLICATIONS

Kohler et al, Nature, vol. 256, Aug. 7, 1975, p. 495–497.
Lu M. et al., Am J Pathol; 123(1):73–8 (Apr. 1986).
Miyawaki S., et al., Arthritis Rheum; 16(6):726–36 (1973).
Davis F. M. et al., Blood; 63(3):676–83 (1984).
Ford R. J. et al., Blood; 63(3):559–65 (1984).
Smetana K., et al., Blut; 46(3):133–41 (1983).
Satoh K., et al., Cancer Res; 43(5):2143–9 (1983).
Chan, P. K. et al., Cancer Res; 40(9):3194–201 (1980).
Reiners J. J. Jr., et al., Cancer Res; 40(5):1367–71 (1980).
Busch, H., et al., Cancer Res; 39(8):3024–30 (1979).
Marashi, F. et al., Cancer Res; 39(1):59–66 (1979).
Davis, F. M., et al., Cancer Res; 38(7):1906–15 (1978).
Chatterjee, A., et al., Cancer Res; 47(4):1123–9 (Feb. 1987).
Freeman, J. W., et al., Cancer Res; 47(2):586–91 (Jan. 1987).
Freeman, J. W., et al., Cancer Res; 46(7):3593–8 (Jul. 1986).
Freeman, J. W., et al., Cancer Res; 45(11 Pt 2):5637–42 (Nov. 1985).
Baak, J. P., Histopathology; 9(4):437–44 (Apr. 1985).
Hashimoto C., et al., J Biol Chem; 258(3):1379–82 (1983).
Lischwe M. A., et al., J Biol Chem; 260(26):14304–10 (Nov. 1985).
Davis F. M., et al., Proc Natl Acad Sci USA; 76(2):892–6 (1979).
Busch R. K., et al., Proc Soc Exp Biol Med; 168(1):125–30 (1981).
Rusch H., et al., Adv Exp med Biol; 92:125–80 (1977).
Love R., et al., Ann Clin Lab Sci; 4(3):131–8 (1974).
Mamaev N. N., et al., Biull Eksp Biol Med; 99(4):477–9 (Apr. 1985) (Published in Russian).
Busch H., et al., Cancer Invest; 1(1):25–40 (1983).
Spohn W. H., et al., Cancer Invest; 3(4):307–20 (1985).
Kelsey D. E., et al., Cancer Lett; 12(4):295–303 (1981).
Busch H., et al., Cardiovasc Res Cent Bull; 19(3):61–99 (1981).
Todorove I.T., et al., Cell Biol Int Rep; 11(3):181–7 (Mar. 1987).
Busch H., et al., Cell Biophys; 2(4):315–25 (1980).
Busch H, et al., Clin Immunol Immunopathol; 18(2):155–67 (1981).
Trent J. M. et al., Cytogenet Cell Genet; 30(1):31–8 (1981).
Steele R. E., et al., Dev Biol; 102(2):409–16 (1984).
Kamata T., et al., Int J Cancer; 34(5):657–65 (1984).
Reichlin M., et al., J Clin Immunol; 4(1):40–4 (1984).
Davis F. M., et al., J Immunol Methods; 59(3):349–57 (1983).
Pazourek J., Neoplasma; 26(2):201–4 (1979).
Tannenbaum M., et al., Urology; 19(5):546–51 (1982).
Ahn et al., Biochemistry 24: 7296–7302 (1985).
Davis et al., J. Immunol. Med. 58:349, "Detection of Leukemic Cell Colonies in Agar Plates by Immunostaining for Human Malignancy-Associated Nucleolar Antigen" (1983).
Davis et al., Proc. Natl. Acad. Sci. USA 76:892, "Nucleolar Antigen Found in Several Human Tumors but not in the Nontumor Tissues Studied" (1979).
American Journal of Pathology, "A Selected Bibliography with Abstracts Pertaining to Nucleolar Antigens".
Freeman et al., Cancer Research 45:5637 (1985).

Primary Examiner—David M. Naff
Assistant Examiner—Florina B. Hoffer
Attorney, Agent, or Firm—Arnold, White & Durkee

[57] ABSTRACT

Tumor nucleoli were treated with polyclonal antisera to normal human tissue nucleoli to block determinants common to tumor and normal tissue nucleoli. Immunization of mice with these immune-complexes resulted in the development of a monoclonal antibody (FB2) to a novel nucleolar proliferation associated antigen which has a molecular weight of about 120 kD and a pI of about 4.5. By indirect immunofluorescence, antibody FB2 produced bright nucleolar staining in a variety of malignant tumors, including cancers of the breast, liver, gastrointestinal tract, genitourinary tract, blood, lung and brain. Specific nucleolar immunofluorescence was not detectable in most normal tissues, although it was weakly detectable in some proliferating nonmalignant tissues including spermatogonia of the tests, ductal regions of hypertrophied prostate, and PHA stimulated lymphocytes. Disclosed are characterizations and methods for isolating nucleolar antigen p120, characterizations and methods for producing antibodies including monoclonal antibody having binding specificity to nucleolar antigen p120, and diagnostic procedures and kits useful for detecting human cancer cells.

13 Claims, No Drawings

DETECTION OF HUMAN CANCER CELLS WITH ANTIBODIES TO HUMAN CANCER NUCLEOLAR ANTIGEN P120

The present invention was made with partial support from Federal funding grants. Subject to these grants, the Government may exercise certain rights in the invention.

FIELD OF THE INVENTION

This invention relates to nucleolar antigens found in a broad range of human cancers and not found in corresponding non-tumor tissues and to antibodies specific to this nucleolar antigen for diagnostic purposes.

BACKGROUND OF THE INVENTION

It has long been known that pleomorphism and hyperactivity of the nucleolus is a major characteristic of cancer cells. These observations prompted studies to determine if tumor nucleoli possess components that are absent from nucleoli of normal cells. After a number of studies using polyclonal antisera to tumor nucleoli demonstrated antigenic differences between tumor and normal tissue nucleoli, efforts are made to purify and characterize specific tumor associated nucleolar antigens.

Chan et al. (*Transplant Proc.* 8: 1955-1957 (1981); *Cancer Res.* 40: 3194-3201 (1980); *J. Cancer Research Clin. Oncol.* 103: 7-16 (1981)) and Takahashi et al. (*J. Cancer Res. Clin. Oncol.* 105: 67-75 (1983)) purified nucleolar proteins with molecular weights of 54, 61 and 68 kD from rat and human tumors that were not found in normal tissues. A nucleolar antigen, p145, was found to be associated with proliferating cells (Freeman et al., *Cancer. Res.* 46: 3593-98 (1986)). The p145 nucleolar antigen was found in a broad range of human tumors but was not detected in most normal resting tissues.

Studies by others (Bravo et al., *Exp. Cell Res.* 136: 311-315 (1981); Celis et al., *Leukemia Res.* 10: 237-249 (1986); Chan et al., *Cell Biol. Int. Rep.* 9: 61-68 (1985); Mathews et al., *Nature* 309: 374-376 (1983); Smetana et al., *Blut* 46: 133-141 (1983); Smetana et al., U.S. Pat. No. 4,448,890; Tan, E. M. *Adv. Immunol.* 33: 167-240 (1982)) using human autoimmune sera detected nuclear and nucleolar antigens in tumor cells and normal growing cells that were not found in normal resting tissues. These antigens are referred to as "proliferating cells nuclear antigens". The best characterized "proliferating cell nuclear antigen" is a 36 kD antigen termed "Cyclin".

SUMMARY OF THE INVENTION

The present invention resides in the surprising and unexpected discovery that a common nucleolar antigen (p120) is found in a broad range of human cancer cells but is not detected in normal human cells. The p120 antigen is characterized as a human cancer cell associated nucleolar antigen which is substantially purified form has a pI on isoelectric focusing ranging from about 4.1 to 4.8, has a molecular weight of about 120,000±5,000 daltons as measured by polyacrylamide gel electrophoresis, is primarily localized in nucleoli of human cancer cells, and has at least 15 tryptic peptides. The p120 antigen is a protein which may have gene control or other functions and is persistent throughout mitosis in a perichromosomal location. Important aspects of the present invention are the discovery of a common nucleolar antigen p120 found in human cancer cells, isolation and purification of this nucleolar antigen, production of monoclonal antibodies specific to this antigen, diagnostic test methods using monoclonal antibodies specific to this antigen to detect human cancer cells, a diagnostic kit containing monoclonal antibodies specific to the nucleolar antigen p120.

DETAILED DESCRIPTION OF THE PREFERRED EMBODIMENTS

The present invention resides in the discovery that a common specific nucleolar p120 antigen is present in the nucleoli of a wide range of human cancer cells, the extraction, isolation, and substantial purification, the production of monoclonal antibodies of high specificity and selectivity to this nucleolar antigen which can be tagged directly or indirectly to allow diagnostic testing for human cancers in vitro and in vivo.

Human Tumors and Other Tissues

All steps for obtaining and analyzing samples in human tissue, blood and serum of suspected cancer patients were approved by the Human Research Committee at Baylor College of Medicine, Houston, Tex. and affiliated hospitals. Sections of human tumors were obtained from frozen sections of surgical specimens, biopsy, or preserved cryostat specimens, mainly from the Department of Pathology, from the Houston Veterans Administration Medical Center and also from The Methodist Hospital, Houston, Tex. These sections were analyzed for the presence of nucleolar antigens including p120 by indirect immunofluorescence.

Preparation of HeLa Cell Nucleoli

Antigen preparation was performed as generally described in an earlier publication, Freeman et al., *Cancer Research* 45: 5637-5642 (1985) herein incorporated by reference to those techniques described.

Briefly, HeLa cells were grown under conditions described in Davis et al., *Proc. Natl. Acad. Sci. USA* 76: 892-896 (1979) and collected from spinner culture bottles (7-8 liters). The cells should be and were in log phase $7-8 \times 10^5$ cell/ml. The cells were centrifuged at $800 \times g$ for eight minutes to form cell pellets. The cell pellets were suspended in (PBS) phosphate buffered saline (0.15M NaCl, 0.01M phosphate, pH 7.2) by gentle homogenization with a loose Teflon pestle and centrifuged at $800 \times g$ for eight minutes. The cells were washed a second time with PBS and the cell pellets were weighed.

The cell pellets were suspended by gentle homogenization in 20 volumes of modified (RSB) reticulocyte standard buffer, 0.01M TRIS, 0.01M NaCl, 0.008M Mg acetate, pH 7.4 and allowed to swell for 30 minutes on ice. The cells were then centrifuged at $1000 \times g$ for eight minutes and resuspended by gentle homogenization in 20 volumes RSB buffer containing 0.5% Nonidet P40. The cells were homogenized with a Dounce homogenizer 20-60 strokes until the cells were broken and the nuclei released and freed of cytoplasm. The cells were then centrifuged $1000 \times g$ for eight minutes, resuspended by gentle homogenization in 0.88M sucrose, 5.0 mM Mg acetate ($20 \times$ weight-volume) and centrifuged at $1500 \times g$ for 20 minutes. The resulting pellet contained the HeLa nuclei that were used to prepare the nucleoli.

For isolation of nucleoli, the nuclear pellet as prepared above was next suspended by gentle homogenization in 0.34M sucrose, 0.5 mM Mg acetate using 2 ml of sucrose for each gram of original cells. The nuclei were sonicated (with a Branson sonifier) by 10-second bursts (and 10 seconds rest). Total time was between 60 and 110 seconds. The nucleoli released were monitored by microscopic examination. To visualize the nucleoli, they were stained with Azure C (the solution consists of 1% Azure C in 0.25M sucrose). The preparation should be and was free of nuclei at the end of the sonication period. The sonicated fraction was underlayed with three times the volume of 0.88M sucrose (without Mg acetate) and centrifuged 1500×g for 20 minutes. The resulting pellet contained the HeLa nucleoli which was used as the immunogen.

Satisfactory purification has usually resulted with the above procedure, and light microscopy showed the quality of these preparations was essentially satisfactory. The key problem in adequate purification of these preparations is the limited amount of original HeLa cells in the cultures which limit the number of repurification steps. Nucleoli prepared from 5 g to 10 g HeLa cell preparations provided sufficient material for adequate purification.

Immunomasking, Immunization and Development of Monoclonal Antibodies

Immunization of total nucleolar protein extracts for the production of antibodies frequently yields antibodies to immunodominant nucleolar antigens found in both tumor and nonmalignant cells. To circumvent these problems, immunomasking techniques were used to develop antiserum with tumor specificity. The techniques employed are more fully described in our earlier publication, Freeman et al., *Cancer Research* 45: 5637-5642 (1985).

For each injection (of five mice), nucleoli isolated from 5 g of HeLa cells were suspended in 1 ml of 0.01M Tris-HCl, pH 7.2, containing 5 mM EDTA and placed in an ice bath for one hour. To mask non-tumor antigens, the unfolded nucleolar structures were treated with anti-normal human liver antisera from two rabbits (10 µl of each antiserum) and allowed to tumble overnight at 4°.

Female Balb/c mice were given four to six primary intraperitoneal injections at monthly intervals of the immune complex described above. The initial injection was given in complete Freund's adjuvant; subsequent injections were given in incomplete Freund's adjuvant. One month after the last primary injection, mice were given a final series of injections over three consecutive days. The mice were injected each day with 400 µg of nucleolar extract or similar amounts of immune complexes in saline with injections given 50% i.v. and 50% i.p. On day four, the mice were sacrificed and spleen cells were collected for fusion.

Cell Fusion and Cloning

Lymphocytes from mouse spleens were collected from a Ficoll-Hypaque gradient (M.A. Bioproducts, Walkersville, MD) and fused with P3-X63-Ag8.653 myeloma cells (Salk Institute, San Diego, CA). For each fusion, approximately $5 \times 10^7$ spleen lymphocytes were added to a 50 ml sterile conical tube containing $2.5 \times 10^7$ myeloma cells. The cells were mixed and washed once in serum free Dulbecco's modified Eagle's medium (DMEM, M.A. Bioproducts). The medium was removed and replaced with 0.1 ml of 50% polyethylene glycol (PEG) 1500 (M.A. Bioproducts) in DMEM. The PEG was mixed with the cells using a large bore pipet (10 ml) for one minute and 7 ml of DMEM was added and allowed to set for five minutes. An additional 20 ml of medium was added and centrifuged for 15 min at 250 g.

The washed cells were dispersed in 30 ml of DMEM supplemented with 20% fetal calf serum (AMF Biological and Diagnostic Products Co., Seguin, TX), 2 mM L-glutamine, 1 mM pyruvate, 0.55 mM L-arginine, 14 µM folic acid, 0.1 mM hypoxanthine, 0.4 µM aminopterin, 0.27 mM L-asparagine, and 14 µM thymidine. The cell suspension was pipeted into 96-well microwell culture plates, 100 µl/well and incubated at 37° and 5% $CO_2$. An additional 100 µl of medium without aminopterin was added to the wells after one week.

After two to four weeks of culture, the supernatants from wells containing growing cell clones were tested for nucleolar immunofluorescence on HeLa cells, according to procedures described hereinafter.

Immunofluorescence positive wells were recloned by limiting dilution in 96 well plates containing approximately $10^5$ syngeneic spleen cells/well as feeder cells. Wells appearing to produce single colonies were retested for immunofluorescence and were recloned one additional time by limiting dilution. The recloned continuous cell line hybridomas were expanded to 24 well plates containing feeder cell layers and from there to flasks without feeder cells.

Polyacrylamide Gel Electrophoresis And Immunoblotting

Analytical electrophoresis was performed on 7.5% polyacrylamide gels with 1% SDS according to Takacs, B. In., *Immunological Methods*, pp. 81-105, New York: Academic Press, 1979.

Whole HeLa cells or proteins extracted from isolated HeLa nucleoli were dissolved in Laemmli buffer and heated in a 100° heating block for 5 minutes. The dissolved samples were loaded on the gel and electrophoresed for 2 to 3 hours at 40 mA. Gels were stained with Coomassie blue or were transferred to nitrocellulose according to the method of Towbin et al., *Proc. Natl. Acad. Sci. USA* 76: 4350-4354 (1979). Excess binding sites on the nitrocellulose were blocked in 7% chicken serum/3% BSA in PBS. Separately, each of the monoclonal antibodies produced as described above were added as a 1:300 dilution of ascites in a 150 mM NaCl buffer containing 5 mM EDTA/50 mM Tris 0.25% gelatin/0.05% NP-40 at pH 7.4 and incubated for 2 hours at room temperature on a rotary shaker. The nitrocellulose strips were washed for 30 minutes in the same buffer without antibody. A rabbit anti-mouse antibody (1 µl/ml, Cappel, Malvern, PA) was then added to strips and incubated at room temperature for 1 hour with shaking. The strips were then washed, radioiodinated protein A (200,000 cpm/ml) was added and incubated at room temperature for 1 hour. Excess protein A was removed by washing for 2 hours with 1.0M NaCl buffer containing 5 mM EDTA/50 mM Tris/0.25% gelatin/0.4% N-lauroylsarcosine, pH 7.4. The strips were then dried and analyzed by autoradiography.

The continuous cells line hybridomas produced by immumization of mice with the immunomasked nucleoli yielded monoclonal antibody which identified four separate nucleolar antigens. Of these hybridomas, FB2 was selected for further study because it produced monoclonal antibodies which showed preferential staining of some tumor tissues compared to normal tissues. The monoclonal antibody designated FB2 identified a 120±5 kD peptide on immunoblots of HeLa nucleolar proteins and had an IgG$_1$ subtype.

Growth of Hybridomas and Purification of Monoclonal Antibodies to p120

To produce large amounts of antibody, hybridoma clones FB'secreting antibody specific for nucleolar antigen p120 were grown as ascites tumors as follows: Approximately $5 \times 10^5$ hybridoma cells collected from cell culture were injected interperitoneally into mice that had been pretreated with pristane. After approximately one week of tumor growth, mice were tapped daily and ascites fluid collected and centrifuged to remove cells. Antibody was purified from ascites fluid by DEAE Affi-Gel Blue chromatography according to the method of Bruck et al., *J. Immuno. Methods* 53: 313–319 (1982). Purified monoclonal antibody was titrated for optimal immunofluorescence detection of antigen on control HeLa slides. The purified monoclonal antibody FB2 was aliquoted in PBS and stored at −70° C. until used. Collection of monoclonal antibody as described herein offers a substantially purified composition, that is, greater than 90% purity on a weight basis. Of course, it should be recognized that other procedures can be employed to yield antibody, monoclonal as well as polyclonal antibody, in substantially pure form.

A deposit of the hybridoma cell line identified herein as FB2 was deposited on Mar. 6, 1987, 1987 with the American Type Culture Collection (Rockville, Md.), and assigned accession number ATCC-HB 9346.

Immunofluorescence Localization Of p120

Immunocytochemical localization of nucleolar antigen p120 identified by monoclonal antibody FB2 was detected by a modification of the indirect immunofluorescence method of Hilgers et al., *Cancer Research* 32: 98–105 (1972). HeLa cells were grown on slides and fixed for 20 min with 2% formaldehyde in PBS. The cells were then permeabilized with ice cold acetone (−20° C.) for 10 minutes and stored in PBS. Crystat sections of tumors or normal tissues were fixed and permeabilized in acetone for 10 minutes at −20° C. The primary antibody (anti-p120) was used at a dilution of 1:300, ascites:PBS which provided optimal immunofluorescence staining on control HeLa cell slides. A sufficient amount of diluted FB2 monoclonal antibody (25 μl) was placed on cells or tissues and incubated in a humid atmosphere at 37° C. for 1 hour. The slides were washed 2 times for 15 minutes in PBS as above and mouse antibody was detected with FITC conjugated goat anti-mouse Ig (Boehringer Mannheim) diluted 1:50 in PBS.

Immunohistological Studies

The immunoreactivity of the monoclonal antibody to the 120 kD nucleolar antigen (p120) was examined by indirect immunofluorescence in a broad range of malignant and non-malignant tissues and cells (Tables 1 and 2).

TABLE 1
IMMUNOREACTIVITY OF A MONOCLONAL ANTIBODY TO NUCLEOLAR ANTIGEN p120 WITH HUMAN CANCER TISSUES OR CANCER CELLS

| Specimen | No. of samples | Intensity of Nucleolar Immunofluorescence |
|---|---|---|
| Adenocarcinomas | | |
| Primary: Colon | 2 | +++ |
| Primary: Small bowel | 1 | +++ |
| Metastatic: Brain | 1 | ++++ |
| Carcinomas | | |
| Primary: | | |
| Hepatocellular | 1 | +++ |
| Lung | 2 | +++ |
| Nasopharyngeal | 1 | +++ |
| Cervical (Squamous cell) | 1 | +++ |
| Prostate | 2 | +++ |
| Metastatic: | | |
| Skin | 1 | ++++ |
| Lymph node | 1 | ++++ |
| Lymphomas (non Hodgkins) | 5 | +++ |
| Lymphoma (Hodgkins) | 1 | +/− |
| Sarcomas: Kaposi's | 1 | +++ |
| Breast cancer: | | |
| intraductal | 1 | +++ |
| carcinomas | 1 | +/− |
| Leukemia (acute lymphocytic) | 2 | +++ |
| Tumor cell lines | | |
| HeLa | 1 | +++ |
| HL-60 (promyelocytic leukemia) | 1 | +++ |
| Colon tumors: | | |
| Omega | 1 | +++ |
| HCT | 1 | +++ |
| Mosar | 1 | +++ |
| JVC | 1 | +++ |
| GEO | 1 | +++ |

TABLE 2
IMMUNOREACTIVITY OF A MONOCLONAL ANTIBODY TO NUCLEOLAR ANTIGEN p120 WITH NONMALIGNANT HUMAN TISSUES OR CELLS

| Specimen | No. of Specimens | Intensity of Nucleolar Immunofluorescence |
|---|---|---|
| Lymphocytes: | | |
| Untreated | 1 | — |
| PHA treated (72 hrs) | 1 | ++ |
| Bone Marrow | 1 | — |
| Kidney | 3 | — |
| Liver | 3 | — |
| Stomach | 1 | — |
| Gallbladder | 2 | — |
| Brain | 2 | — |
| Lymph Node | 2 | — |
| Spleen | 2 | — |
| Breast | 1 | — |
| Lung | 3 | — |
| Colon | 2 | — |
| Mandibular tissue (inflamed) | 1 | — |
| Prostate[a] | | |
| Hypertrophied | 2 | + (1 of 2) |
| Normal | 2 | — |
| Testes | 1 | +/− trace |

[a]Weak nucleolar immunofluorescence detectable in some ducts.

Bright nucleolar specific fluorescence was detected in a broad range of malignant tumors and cells (Table 1) including cancers of the gastrointestinal tract, genitourinary tract, liver, lung, breast, lymphatics, and blood. Nucleolar immunofluorescence and hence antigen p120 was not detected in corresponding normal tissues (Table 2). In some tissues (i.e. kidney) some general background staining was observed. This type of background fluorescence was also found in specimens to which no primary antibody was added.

In most tumors, monoclonal antibody FB2 produced bright nucleolar immunofluorescence. However, in one Hodgkins lymphoma and one breast tumor only weak nucleolar fluorescence was observed. The lesser immunofluorescence intensity in these tumors may relate to tumor type, staging or response to treatment.

Nucleolar immunofluorescence demonstrating the presence of the p120 antigen was detected in 48 hour phytohemagglutinin (PHA) stimulated lymphotocytes, spermatogonia of the testes and the ductal epithelium of 1 to 2 hypertrophied prostates studied (Table 2). The intensity of staining in these normal proliferating tissues was weaker than that observed for most tumor nucleoli (Table 1).

Extraction of Nucleoli for Antigen Purification

Isolated HeLa nucleoli (0.3 g wet weight) were washed twice with 5 ml 0.075M NaCl/.025M EDTA pH 7.6 and extracted four times with 5 ml 20 mM Tris-HCl, pH 8.0/0.2% w/v sodium deoxycholate. Pellets were suspended using a Dounce homogenizer followed by centrifugation at $25,000 \times g$ for 15 mins. The Tris-DOC extract was then treated with RNAse overnight at 4° (1,000 units each of RNAse T, and A) and then loaded on a 5–45% sucrose density gradients in the same buffer. Other Tris-DOC extracts not treated with RNAse were separated on similar sucrose gradients. All extraction buffers contain 0.1 mM PMSF, 1 µg/ml $B_2$ macroglobulin (Sigma, St. Louis, MO), 1 µg/ml leupeptin and 1 ug/ml aprotinin (Boeringer Mannheim, Indianapolis, IN) to inhibit endogenous proteolytic activity.

Immunoaffinity Chromatography Purification of p120 Antigen

Anti-p120 Ig was isolated from ascites by AffiGel Blue Chromatography using the methods described in Bruck et al., *J. Immuno. Methods* 53: 313–319 (1982) and was coupled to CNBr-activated Sepharose 4B (Pharmacia). Sucrose density gradient fractions of HeLa nucleolar extracts made according to the procedure above and enriched in p120 as determined by enzyme linked immunosorbent assay (ELISA) were combined and dialyzed against 0.01M Tris/0.1% DOC. The dialyzed proteins (approximately 2 mg) were mixed with anti-p120 monoclonal antibody coupled to Sepharose and binding was carried out overnight at 4° by tumbling end over end. The unbound proteins were eluted with 0.1M phosphate buffer containing 0.5M NaCl, pH 7.4 and the bound p120 antigen was eluted with 4M $MgCl_2$. The p120 sample was dialyzed against 1000 volumes of 0.01M Tris-HCl, pH 8.0 and used for ELISA and gel electrophoresis. The resulting nucleolar antigen p120 derived from this procedure was deemed substantially pure in that greater than 90% on a weight basis of an isolated sample comprised the p120 antigen. Of course, it should be recognized by one of ordinary skill in this art that other extractive and purification schemes can be employed to secure substantial purity on the order of greater than 95% w/w purification.

Model Systems for Studying Cell Proliferation

The effect of cell proliferation on the expression of nucleolar antigen p120 was examined in; (a) phytohemagglutinin (PHA) stimulated lymphocytes; (b) retinoic acid induced differentiation of human leukemia HL-60 cells and; (c) HeLa cells growth arrested by serum deprivation.

1. PHA Stimulation of Human Lymphocytes

Isolated human lymphocytes were tested in culture with PHA and examined by immunofluorescence at 24 hour intervals for the detection of antigen p120. Nucleolar antigen p120 was not detected in fresh peripheral blood lymphocytes or in untreated lymphocytes maintained in cultures. Nucleolar antigen was weakly positive or negative in 24 hour PHA treated lymphocytes depending on the experiment. The nucleolar structure was intact in these cells since anti-protein B23 monoclonal antibody (protein B23 in a nucleolar antigen found in tumor and non-tumor cells) produced bright nucleolar specific fluorescence. Nucleolar antigen p120 immunofluorescence reached a maximum intensity in 48 hour PHA treated lymphocytes given small dot-like immunofluorescence within the nucleolus. This result suggests that p120 may be compartmentalized within the nucleolus.

2. HL-60 Cell Differentiation

As an obverse approach to mitogenic stimulation of resting lymphocytes the effect of termination of cell proliferation on antigen p120 expression was studied during retinoic acid induced differentiation in human leukemia HL-60 cells. The HL-60 human promyeolocytic leukemia cell line was grown in suspension cultures in RPMI 1640 medium (Grand Island Biological Co.) containing 10% fetal calf serum, 100 IU penicillin/ml, 100 ug streptomycin/per ml and 2 uM/ml trans-retinoic acid (Sigma). HL-60 cells treated with the retinoic acid were examined for specific immunofluorescence at 24 hour intervals up to 120 hours; the cells were attached to slides by cytocentrifugation. A side-by-side control of untreated HL-60 cells was done at each time.

Untreated control HL-60 cells showed bright nucleolar immunofluorescence staining with the monoclonal antibody FB2, anti-p120. The retinoic acid treated HL-60 cells approximately doubled in number up through 48 hours; between 48 and 72 hours at slight increase in cell number was found with no further increase in cell number between 72 and 96 hours. At 48 hours of retinoic treatment a decrease in the immunofluorescence was observed. At 96 hours a change in morphology from blast cells in untreated culture to more mature neutrophils in treated cells was observed in most cells. Approximately 5% of the cells retained a blast-like appearance.

Immunofluorescence with monoclonal antibody FB2 was not detected in most cells following 96 hours of retinoic acid treatment. Some immunofluorescence was observed in 3 to 5% of the 96 hour retinoic acid treated cells. The immunofluorescent cells had a more blast like appearance. The nucleolar structure of differentiated cells was, however, maintained since all cells stained with the monoclonal antibody to protein B23. These findings suggest that antigen p120 expression is lost simultaneously with cessation of cell cycling.

3. Growth Arrested HeLa Cells

HeLa cells were growth arrested by 48 to 72 hours of serum deprivation to determine whether antigen p120 is directly associated with cell cycling. HeLa cells were grown for 48 hours in DMEM medium containing 10% fetal calf serum in a humidified atmosphere with 5% $CO_2$. After 48 hours, the medium was replaced by a DMEM medium which lacked the fetal calf serum and cultured for another 48 to 72 hours. Following serum deprivation, the medium was replaced with fresh DMEM medium containing 10% fetal calf serum. Samples were collected hourly up to seven hours, except for the first hour when 30 minute samples were collected; at each time the p120 antigen was evaluated by indirect immunofluorescence.

In four separate experiments, decreased nucleolar immunofluorescence was found in 24 hour serum deprived HeLa cells and antigen p120 was not detected after 36 to 72 hours in serum free media.

Following serum replenishment antigen p120 was detected within 30 minutes and increased to its original intensity by 2 hours. This finding indicates that antigen p120 is temporally expressed in the early G1 cell cycle phase.

p120 Antigen Characterization

RNAse treated and non-RNAse treated HeLa cell nucleolar extracts were fractionated separately on 5–45% linear sucrose density gradients. In both extracts, more than 50% of the nucleolar proteins were found near the bottom (>17S) of the gradient. The ELISA analysis of individual gradient functions indicated that p120 immunoreactivity was spread across the gradient. The highest concentration being present was near the bottom (>17S) in both RNAse treated and non-treated extracts.

Fractions from the sucrose gradient of RNAse treated nucleolar extracts were electrophoresed SDS polyacrylamide gels and stained with silver or examined for p120 immunoreactivity by immunoblotting. Most of the p120 immunoreactivity was observed in the higher molecular weight fractions which is in agreement with their higher ELISA activity. A 120 kD peptide was also visualized on silver stained gels in these fractions. These results indicate that p120 is associated with a high molecular size particle that is resistant to RNAse treatment.

The pI of p120 ranged from 4.1 to 4.8 on immunoblots of 2-dimensional polyacrylamide gels. The average pI of p120 was 4.5 as determined by linear regression analysis.

Following the procedures described by Elder et al., *J. Biol. Chem.* 252: 6510–6515 (1977), a tryptic peptide map of radioiodinated p120 from a gel purified band shows that p120 has at least 15 tryptic peptides; one large peptides has rapid mobility.

Nucleolar antigen p120 differs from proliferating cell nuclear antigens, p145, and p40 by molecular size, peptide mapping, and time of cell cycle expression. Like antigen p145, antigen p120 is associated with a particle (2217S). However, the particle containing the p120 peptide is resistant to RNAse treatment while the p145 antigen is readily released by RNAase to a smaller particle (10–20S).

Antigen p120 is expressed rapidly (within 30 minutes) following serum replacement in growth arrested HeLa cells. The presence of p120 has been observed in some experiments as early as 15 minutes following refeeding. Immunofluorescence intensity reached a maximum at 2 hours and persisted throughout the cell cycle. Antigen p145 persists in growth arrested tumor cells and p40 is expressed at 4–6 hours following addition of serum. The proliferating cell nuclear antigen cyclin was reported to be synthesized at the $G_1/S$ border. The early $G_1$ expression of p120 is similar to that reported for the nuclear oncogene c-fos. However, antigen p120 differs from c-fos as well as the nuclear oncogenes c-myc and c-myb in molecular size and its specific nucleolar localization.

Studies with nuclear oncogenes (c-fos c-myc, and c-myb) suggest that the expression of their gene products relates to cell proliferation; they are also expressed temporally at specific time points in the cell cycle. Like antigen p120, c-fos has been reported to be expressed early in $G_1$.

The association of p120 with proliferating cells and its specific time of expression in early $G_1$ suggests it plays a role in cell proliferation. This antigen may be used as a marker for early $G_1$ and may also have immunodiagnostic value as a marker for cell proliferation.

Utility

The hybridoma cell line FB2 and the monoclonal antibodies produced therefrom described herein are useful in the purification and characterization of the tumor specific nucleolar antigen p120. Of course, repeating the procedures described in this application should result in eliciting additional polyclonal and monoclonal antibodies specific for nucleolar antigen p120. These other polyclonal and monoclonal antibodies are characterized as immunospecific for nucleolar antigen p120, although their genetic makeup and specific idiotype may vary from FB2 derived monoclonal antibodies.

The nucleolar nitrogen p120 and anti-p120 antibodies, such as polyclonals derived from antisera or monoclonal antibodies such as that examplified by FB2-monoclonal antibodies, are useful in diagnostic procedures for detecting human cancer tissue or cells.

ALTERNATIVE IMMUNOASSAYS

Although the immunoblot and immunofluorescent assays described herein are effective and give good results, these methods do not necessarily reflect the methods of choice for routine diagnostic procedures in the clinical setting.

The anti-p120 monoclonal antibodies, antisera, or polyclonal antibodies can be used in one or more of other many ways as a diagnostic test. In particular, the antibodies can be tagged by conventional techniques with tracer labels such as, for example, radioisotopes, bioluminescent labels such as luciferase, fluorescent labels, enzymes or biological ligands, such as lectins, avidin or biotin. Such labelled antibodies are extremely useful in diagnostic tests. Various diagnostic approaches to detecting p120 nucleolar antigens can be utilized including both direct and indirect immunoassays. Variations on the general immunoassay theme include radioimmunoassay (direct or indirect), fluorescent antibody techniques (direct or indirect), enzyme- or lectin-linked immunosorbent assays, inhibition of hemolysis assays, inhibition of agglutination tests, agglutination reactions (antibody-ligand mediated), and/or complement consumption tests. The use of one or more anti-p120 antibodies in such systems constitutes an important new and useful test for the detection of p120 nucleolar antigen associated with human cancer cells.

For use in diagnostic kits, label-conjugated or non-conjugated antibodies to p120 may be packaged separately in lyophilized form or dissolved phosphate buffered saline (PBS) or other buffered suspending agents for distribution. Suitable suspending agents include glycerin, heparin, or sucrose. Suitable buffers include barbital buffers, morpholine, buffers, MOPS-3-(N-morpholino) propane sulfonic acid, hepes-N-2-hydroxyethylpiperazine-N-2-ethane sulfonic acid, Tris carbonate and the like.

The foregoing description of the invention has been directed to particular embodiments for purposes of explanation and illustration. It will be apparent, however, to those of ordinary skill in the art that many modifications and changes in the processes of preparing and implementing the described embodiments may be made without departing from the essence of the invention.

What is claimed is:

1. A human cancer cell associated nucleolar antigen substantially in purified form characterized by:
   a pI on isoelectrofocusing of about 4.1 to about 4.8;
   a molecular weight of about 120,000±5,000 daltons as measured by polyacrylamide gel electrophoresis;
   being primarily localized in nucleoli of human cancer cells, but not detected in normal, non-proliferating cells;
   being expressed in the early $G_1$ cell cycle phase; and
   having a binding specificity to antibody derived from hybridoma ATCC HB 9346 deposit.

2. Antibody having binding specificity to nucleolar antigen p120, which nucleolar antigen is characterized by:
   a pI on isoelectrofocusing of about 4.1 to about 4.8;
   a molecular weight of about 120,000±5,000 daltons as measured by polyacrylamide gel electrophoresis;
   being primarily localized in nucleoli of human cancer cells, but not detected in normal, non-proliferating cells;
   being expressed in the early $G_1$ cell cycle phase; and
   having a binding specificity to antibody derived from hybridoma ATCC HB 9346 deposit.

3. The antibody of claim 2 which is a monoclonal antibody.

4. The antibody of claim 2 which is derived from continuous cell line ATCC HB 9346 deposit.

5. The antibody of claim 2 which has been produced with nucleoli isolated from HeLa cells.

6. A continuous cell line which produces a monoclonal antibody having binding specificity to nucleolar antigen p120, which nucleolar antigen is characterized by:
   a pI on isoelectrofocusing of about 4.1 to about 4.8;
   a molecular weight of about 120,000±5,000 daltons as measured by polyacrylamide gel electrophoresis;
   being primarily localized in nucleoli of human cancer cells, but not detected in normal, non-proliferating cells;
   being expressed in the early $G_1$ cell cycle phase; and
   having a binding specificity to antibody derived from hybridoma ATCC HB 9346 deposit.

7. The continuous cell line of claim 6 which is a clone of ATCC HB 9346 deposit.

8. A process for the immunological detection of cancer in human tissue or cell specimens comprising:
   contacting specimens with antibody characterized by binding specificity to nucleolar antigen p120 and detecting the localization of said antibody in the nucleoli of malignant cells but not normal cells of said specimen as a measure of cancer.

9. A diagnostic kit for performing immunoassays for detecting the presence of nucleolar antigen p120 which comprises multiple containers wherein one of said containers has therein antibody having binding specificity to nucleolar antigen p120.

10. The diagnostic kit of claim 9 wherein the antibody is antisera.

11. The diagnostic kit of claim 9 wherein the antibody is a monoclonal antibody.

12. The diagnostic kit of claim 9 wherein the antibody is monoclonal antibody derived from hybridoma clone, ATCC HB 9346 deposit.

13. The diagnostic kit of claim 9 wherein the antibody is conjugated with a label.

* * * * *